United States Patent [19]

Sugawara

[11] Patent Number: 5,347,362
[45] Date of Patent: Sep. 13, 1994

[54] BONDING WIRE INSPECTION METHOD

[75] Inventor: Kenji Sugawara, Tokyo, Japan

[73] Assignee: Kabushiki Kaisha Shinkawa, Tokyo, Japan

[21] Appl. No.: 983,661

[22] Filed: Dec. 1, 1992

[30] Foreign Application Priority Data

Dec. 2, 1991 [JP] Japan .................. 3-341834

[51] Int. Cl.$^5$ ............................................. G01B 11/00
[52] U.S. Cl. ..................................... 356/372; 356/384
[58] Field of Search ................................ 356/372, 384

[56] References Cited

U.S. PATENT DOCUMENTS 4,942,618  7/1990  Sumi et al. .......................... 356/384

FOREIGN PATENT DOCUMENTS 2-129942  5/1990  Japan .
3-76137   4/1991  Japan .

Primary Examiner—F. L. Evans
Attorney, Agent, or Firm—Koda and Androlia

[57] ABSTRACT

A method of inspecting wires bonded between the pads of a semiconductor chip and the leads of a lead frame taking the steps of: bringing the focus of an optical assembly into a desired point of a bonded wire, thus obtaining the height of such a desired point of the wire as a reference; photographing an image of the wire at the reference height; and then obtaining the height of the wire based upon the amount of the indistinct image of the photographed wire.

3 Claims, 7 Drawing Sheets

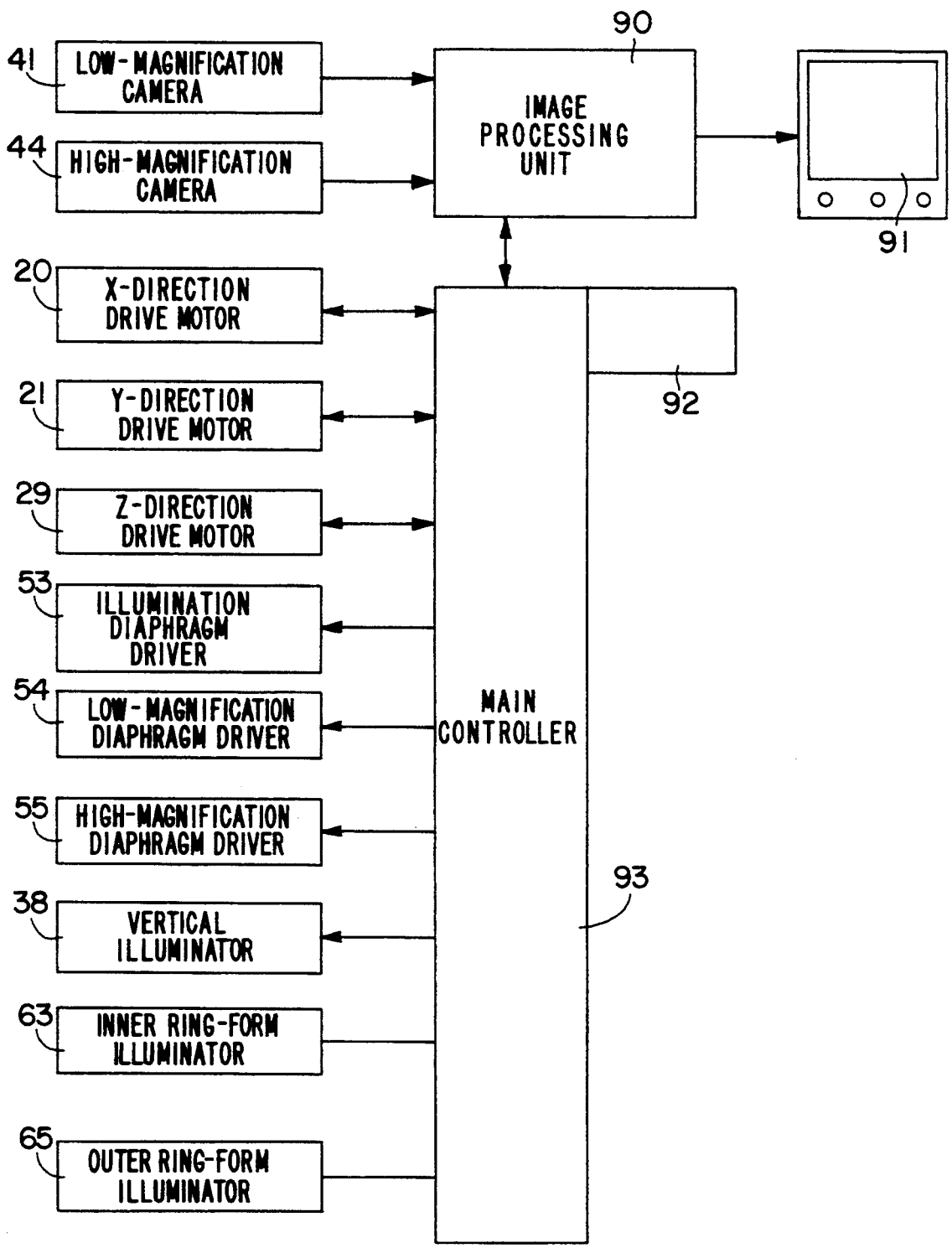
F I G. 6

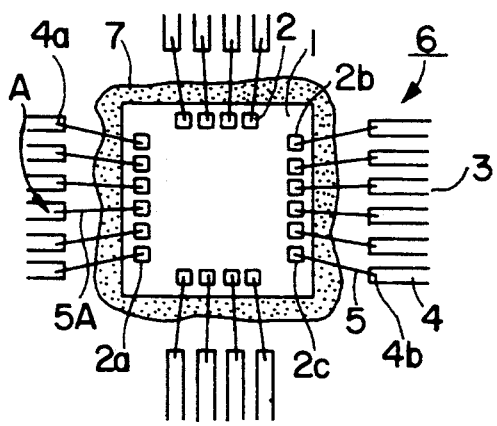
F I G. 15
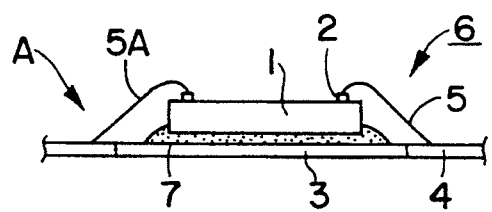
F I G. 16
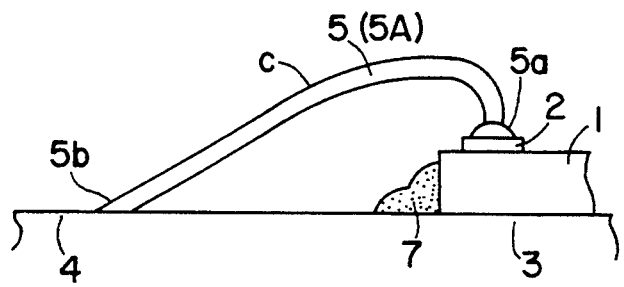
F I G. 17
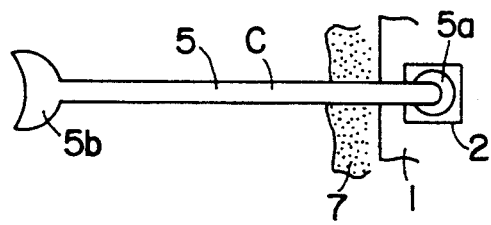
F I G. 18

BONDING WIRE INSPECTION METHOD

BACKGROUND OF THE INVENTION

1. Field of the Invention

The present invention relates to a bonding wire inspection apparatus for inspecting wires bonded between the pads of semiconductor chips and the leads of lead frames.

2. Prior Art

FIGS. 15 through 18 show a sample 6 that is an example to be inspected. The sample 6 includes wires 5 that are bonded between the pads 2 of a semiconductor chip 1 and the leads 4 of a lead frame 3. In these Figures, reference numeral 7 indicates squeezed out paste that is used for bonding the semiconductor chip 1 to the lead frame 3. FIG. 19 shows one of the conventional inspection apparatuses.

As shown in FIG. 19, a vertical illuminating means 11 is located above the sample 6, which is placed on an inspection stand 10. The vertical illuminating means 11 is installed at the bottom of an optical means 12. A CCD camera 13, that consists of a CCD (photoelectric converter element) and a drive section therefor, is mounted on the top of the optical means 12. The CCD outputs an image signal that is an image of the sample 6 taken in by the optical means 12. The image signal from the CCD camera 13 is processed by an image-processing arithmetic unit 14, and the shape of the wire 5 is recognized and the bonded position of the wire 5 is measured.

The optical means 12, that includes the vertical illuminating means 11 and the CCD camera 13, is provided on an X-Y table 15. Inside the vertical illuminating means 11, a half-mirror 16 is installed so that the half-mirror 16 is beneath the CCD camera 13. Also inside the vertical illuminating means 11 are a condensing lens 17 and a light bulb 18 that are installed on one side of the half-mirror 16.

The bonding wire inspection apparatus of this type is described in, for example, Japanese Patent Application Laid-Open (Kokai) Nos. 2-129942 and 3-76137.

In the apparatus shown in FIG. 19, when the vertical illuminating means 11 is switched on, the light from the light bulb 18 passes through the condensing lens 17, is reflected by the half-mirror 16, and then vertically directed onto the sample 6. Then, the X-Y table 15 is moved so that the CCD camera 13 is positioned above the object of inspection or the sample 6, and the image signal (that represents microscopic parts of the object of inspection, such as the ball and crescent at both ends of a bonded wire) obtained by the CCD camera 13 is subjected to noise removal, edge enhancement in the inspection area and enlargement or reduction of the image, etc. by means of the image-processing arithmetic unit 14, thus enhancing (restoring) the image of the microscopic parts of the object of inspection so that the image is easier to see. Afterward, the inspection and measurement operations are performed.

When the microscopic parts of the object of inspection are thus optically imaged, the magnification of the optical means 12 is set at a high value. For example, the magnification is set to be 2 to 3 times larger when a ⅔-inch CCD camera is used.

Conventionally, though not disclosed in the Laid-Open prior art listed above, when a part of the object of inspection is focused, an opto-head that contains the vertical illuminating means 11, the optical means 12 and the CCD camera 13 is raised and lowered as a whole in the Z direction (or in a vertical direction) by a Z-direction drive motor.

For instance, when the wire height at point C in FIGS. 17 and 18 is measured, the opto-head as a whole is first raised or lowered so that the surface of the semiconductor chip 1 is focused, and then using this point as a reference, the opto-head is again raised or lowered as a whole so that the focus is brought into the point C of the wire 5. The height of the point C of the wire 5 is, therefore, obtained from the amount of movement of the opto-head that has moved from where the reference value has been on the surface of the semiconductor chip 1.

In the prior art described above, the measurement of wire height is performed only on one point of the imaged object. Accordingly, when the height of, for example, the entire wire is measured, numerous points on the wire need to be focused by moving up and down the optical means along the wire, thus obtaining the height of each one of the points. Thus, it takes time even though computers are used to process the information of the obtained heights.

SUMMARY OF THE INVENTION

Accordingly, it is an object of the present invention to provide a bonding wire inspection method that can greatly reduce the time for measuring the height of a bonded wire.

The object of the present invention is accomplished by a unique method that inspects the wires bonded between the pads of a semiconductor chip and the leads of a lead frame in which: the focus of an optical means is first brought into a desired point of the object of inspection, which is a bonded wire; then using a Z-direction height at this desired point, that is thus focused, as a reference, an image of the desired point is photographed by a camera; and then finally the height of the wire is obtained from the indistinct image widths of the photographed image.

When the focus of the optical means is brought into a particular point of the bonded wire, the image of the wire, that has been taken into the optical means and image-processed by an image processor, appears indistinctly with differences in the width. Thus, such an indistinct image width (or vignette) of the wire is measured by a main controller.

Experiments show that there is a constant relationship between the amount (or width) of an indistinct (vignette) image of the object and the actual height of the object. Accordingly, by measuring the indistinct image width of the wire by a main controller, the height of a particular point of the wire can easily be measured.

If the amount of indistinctness of the image (or the vignette) becomes larger, the differences in the relative brightness between the indistinct image and the area around the image also becomes smaller, thus making it difficult to recognize the image of the object. In this case, the focal point of the optical means is moved up and down so that the indistinct image of the object is taken in at the moved point.

By combining the indistinct images taken in at different focal positions, it is possible to conduct a more precise image recognition.

As seen from the above, since the height of the object of inspection (wire) is measured with fewer focusing actions, the time for a height measurement can be greatly shortened.

BRIEF DESCRIPTION OF THE DRAWINGS

FIG. 6 is a block diagram of the control circuit of the bonding wire inspection apparatus shown in FIG. 1;

FIG. 15 is a top view of a wire-bonded semiconductor device;

FIG. 16 is a front view thereof;

FIG. 17 is an enlarged front view of the wire bonded to the pad of a semiconductor device;

FIG. 18 is a top view thereof; and

DETAILED DESCRIPTION OF THE INVENTION

One embodiment of the present invention will be described with reference to FIGS. 1 through 6. In these Figures, parts that are the same as those in FIGS. 15 through 18 are given the same symbols, and a detailed description of those parts is omitted.

Figure 1:
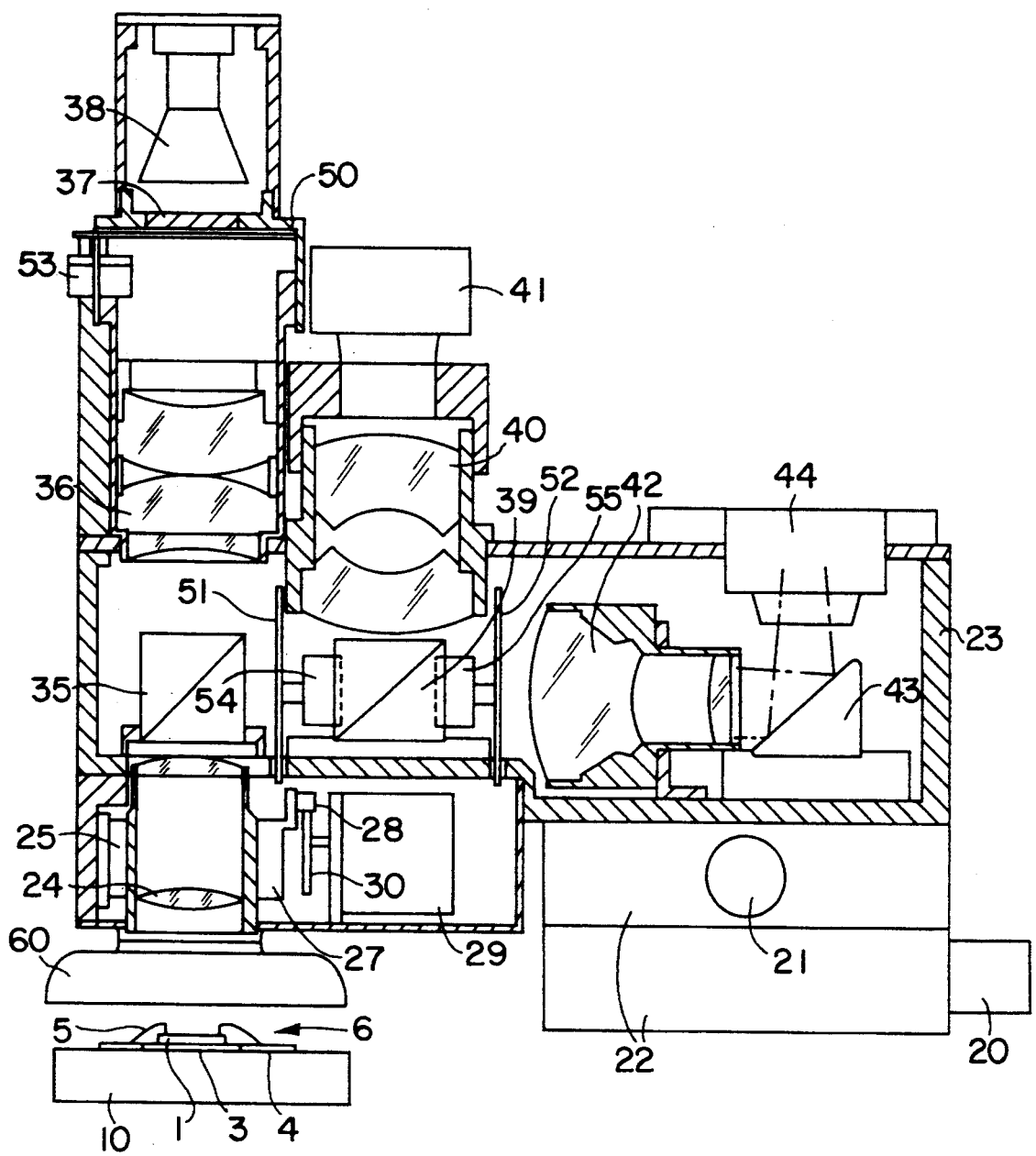
FIG. 1 is a cross section of a bonding wire inspection apparatus used for the inspection method of the present invention.

As seen from FIG. 1, an opto-head 23 is mounted on an X-Y table 22 which is driven in the X and Y (or horizontal) directions by an X-direction drive motor 20 and a Y-direction drive motor 21, respectively.

Figure 2:
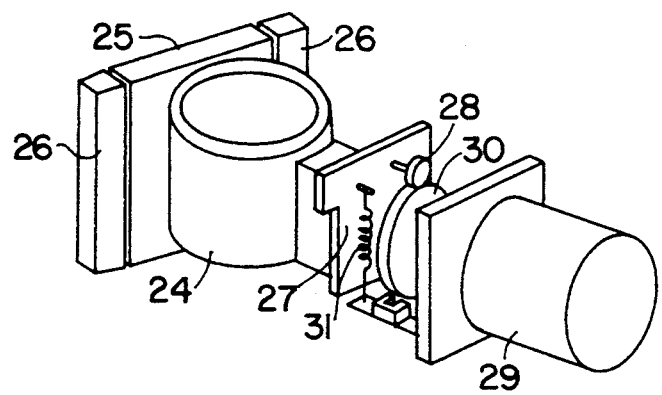
FIG. 2 is a perspective view of the Z-direction driving means for the objective lens group used in the apparatus of FIG. 1.

The opto-head 23 has an objective lens group 24 which is installed so as to face an inspection stand 10. As shown in FIGS. 1 and 2, the objective lens group 24 is mounted to a linear slider 25. The linear slider 25 is installed so that it can move up and down along a pair of linear gauges 26 which are fixed to the opto-head 23. The objective lens group 24 is also attached to a roller-supporting plate 27, and a roller 28 is rotatably mounted on the roller-supporting plate 27. In addition, a Z-direction drive motor 29 is installed in the opto-head 23. A cam 30 is attached to the output shaft of the Z-direction drive motor 29, and the roller-supporting plate 27 is urged downwardly by a spring 31 so that the roller 28 is in contact with and presses against the cam 30.

As shown in FIG. 1, a first half-prism 35, which is used to split light, is installed above the objective lens group 24, and an illumination lens group 36 is installed above the first half-prism 35. In addition, a diffusing plate 37 is installed above the illumination lens group 36, and a vertical illuminator 38 is installed above the diffusing plate 37.

A second half-prism 39 is installed next (on the right side in FIG. 1) to the first half-prism 35, and a low-magnification imaging lens group 40 is installed above the second half-prism 39. Furthermore, a low-magnification camera 41 is installed above the low-magnification imaging lens group 40.

Reference numeral 42 refers to a high-magnification imaging lens group which is installed next (on the right side in FIG. 1) to the second half-prism 39, and a reflecting mirror 43 is installed next (on the right side in FIG. 1) to the high-magnification imaging lens group 42. Furthermore, a high-magnification camera 44 is installed above the reflecting mirror 43.

Diaphragms 50, 51 and 52 that are electrically operated are respectively installed beneath the vertical illuminator 38, between the first and second half-prisms 35 and 39, and between the second half-prism 39 and the high-magnification imaging lens group 42. These electrically operated diaphragms 50, 51 and 52 are respectively driven by an illumination diaphragm driver 53, a low-magnification diaphragm driver 54 and a high-magnification diaphragm driver 55, and the opening diameters of the diaphragms 50, 51 and 52 are altered accordingly. The electrically operated diaphragms 50, 51 and 52 are similar to diaphragms used in, for example, ordinary cameras.

The diaphragm 50 controls the angle of illumination of the vertical illuminator 38 with respect to the object of inspection or the sample 6. The diaphragm 51 adjusts the opening diameter of the objective lens group 24. In other words, the diaphragm 51 adjusts the focal depth for the objective lens group 24. The diaphragm 52 equalizes the brightness obtained at high and low magnification rates.

The opto-head 23 has a ring-form illumination assembly 60. The illumination assembly 60 is positioned so that it is under the objective lens group 24.

Figure 3:
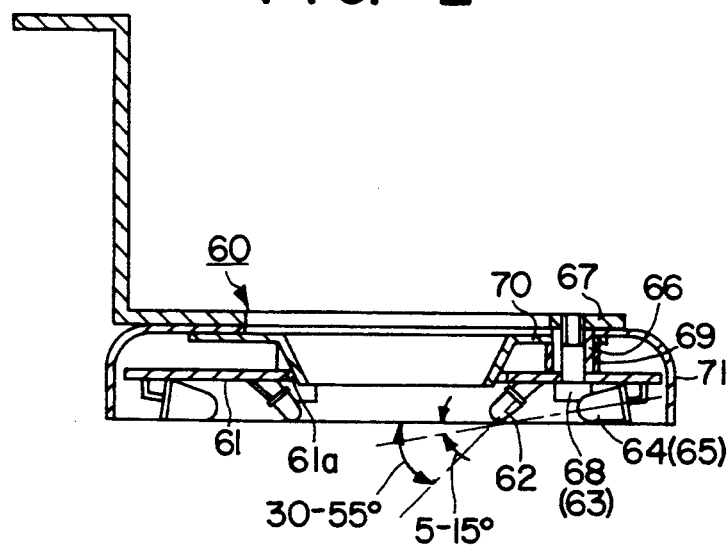
FIG. 3 is a cross section of the ring-form illumination assembly used in the apparatus shown in FIG. 1.
Figure 4:
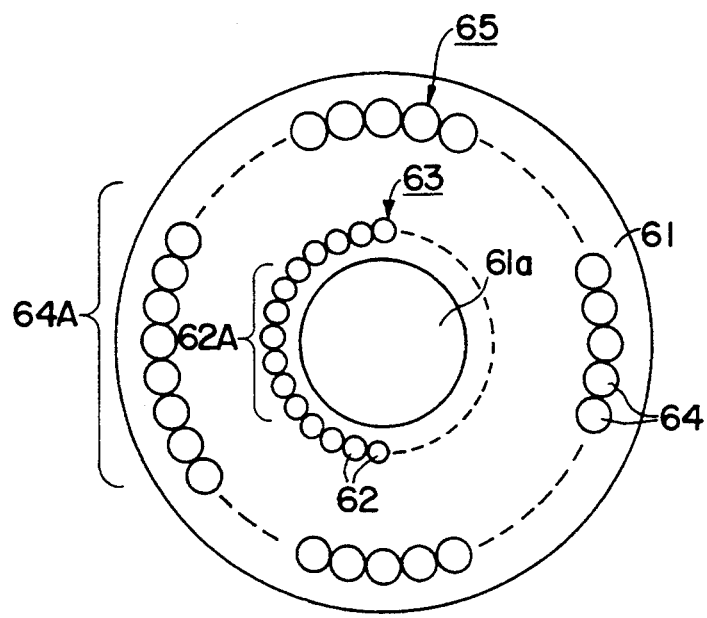
FIG. 4 illustrates the layout of the LED's used in the ring-form illumination assembly shown in FIG. 3.

The ring-form illumination assembly 60, the detail thereof being shown in FIGS. 3 and 4, comprises an inner ringform illuminator 63 that has a high illumination angle and an outer ring-form illuminator 65 that has a low illumination angle.

The inner ring-form illuminator 63 is made up of plural LED's 62 installed in the form of a ring or circle. The LED's 62 are mounted to an illumination holding plate 61 so that they are around the center opening 61a of the holding plate 61. The outer ring-form illuminator 65 is also made up of plural LED's 64 mounted to the illumination holding plate 61. The LED's 64 of the outer ring-form illuminator 65 are arranged in the form of a ring or circle around the inner ring-form illuminator 63.

The respective circular rows of LED's 62 and 64 face toward the optical axis of the vertical illuminator 38. The LED's 62 of the inner ring-form illuminator 63 are inclined at an angle of approximately 30 to 55 degrees relative to a horizontal level, thus having a high illumination angle. The LED's 64 of the outer ring-form illuminator 65 are inclined at an angle of approximately 5 to 15 degrees relative to the horizontal level, thus having a low illumination angle.

An attachment plate 67 is mounted on the illumination holding plate 61 via a supporting column 66, and the illumination holding plate 61 is fastened to the attachment plate 67 by a screw 68 that is inserted into the supporting column 66. A spacer 69 is fitted over the supporting column 66, and a light-screening plate 70 and a cover 71 are installed between the spacer 69 and the attachment plate 67.

In FIG. 3, only the right and left side LED's 62 and 64 are shown; and in FIG. 4, some of the LED's 62 and 64 are omitted with those omitted LED's shown by broken lines.

Figure 5:
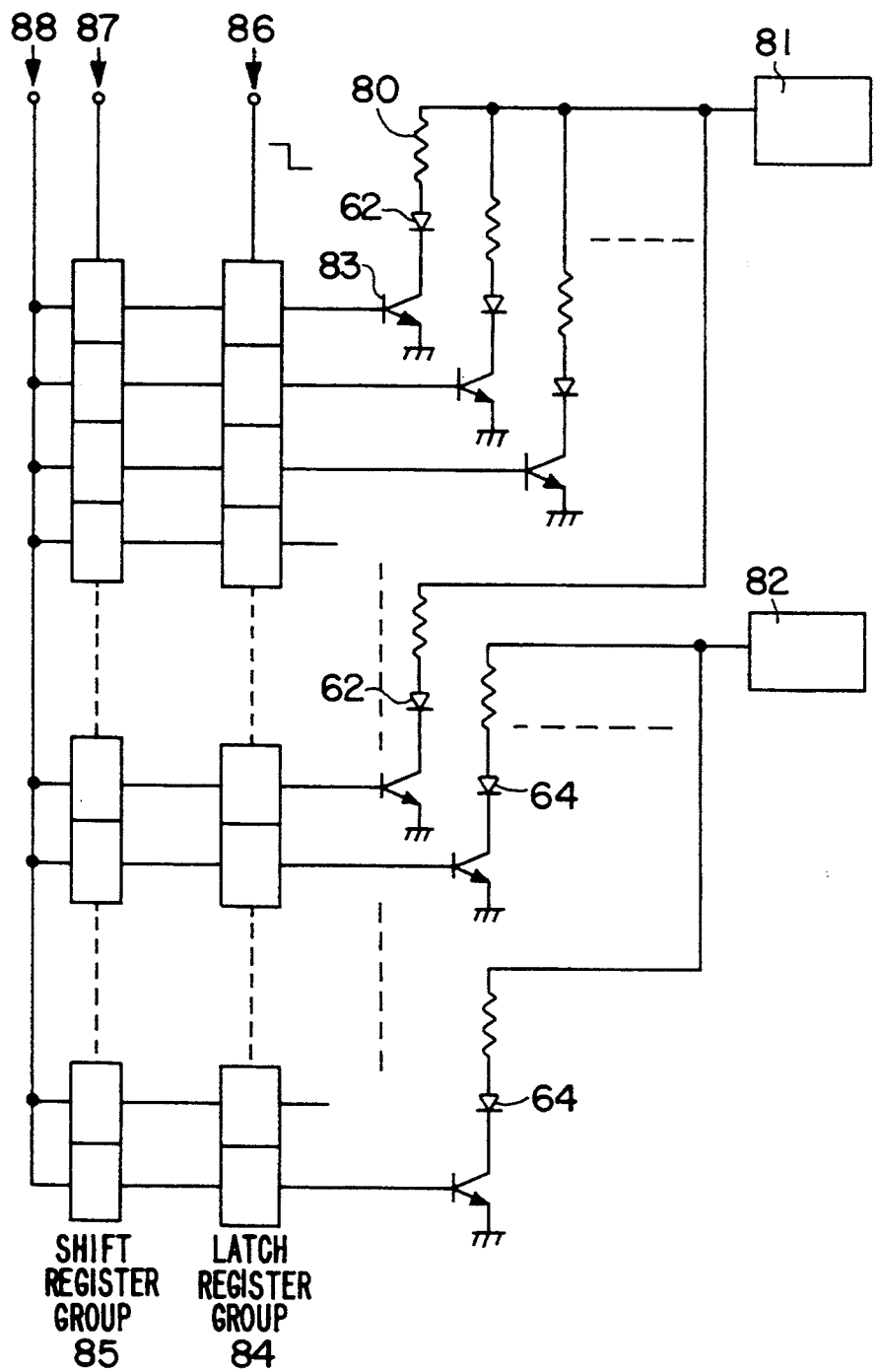
FIG. 5 is a block diagram of the illumination switching circuit for the ring-form illumination assembly.

The LED's 62 and 64 of the inner and outer ring-form illuminators 63 and 65 are operated by an illumination switching circuit that is shown in FIG. 5.

In FIG. 5, one end of each of the LED's 62 and 64 is connected to a programmable constant-voltage circuit 81 via a resistance 80, while another end of each LED is connected to the collector of a transistor 83. The emitters of the transistors 83 are grounded, and the bases of the transistors 83 are connected to a shift register group 85 via a latching register group 53. A load signal 86 is inputted into the latching register group 84, a high-low (H-L) input signal 87 is inputted into the shift register group 85, and a clock signal 88 is inputted into each shift register of the shift register group 85.

As shown in FIG. 6, the low-magnification camera 41 and the high-magnification camera 44 convert the obtained images into electrical signals and send those signals to an image processing unit 90. The images are processed by the image processing unit 90 and displayed on a monitor 91. The processed images are also sent to a main controller 93 which has a memory 92. Furthermore, via the signals from the main controller 93, the image processing unit 90 is operated.

The X-direction drive motor 20, the Y-direction drive motor 21, and the Z-direction drive motor 29 are all controlled by the main controller 93; and positional signals from the X-, Y-, and Z-direction drive motors 20, 21, and 29 are sent to the main controller 93. In addition, the illumination diaphragm driver 53, the low-magnification diaphragm driver 54, the high-magnification diaphragm driver 55, the vertical illuminator 38, the inner ring-form illuminator 63 and the outer ring-form illuminator 65 are all controlled by the main controller 93.

Next, the operation of the embodiment will be described below.

Prior to the commencement of actual inspection, opto-head information is inputted, as described below, into the memory 92 and stored therein. First, a sample that is the same type as the object of inspection (sample 6) is selected, and alignment points and alignment images for calculating the positions of the pad 2 and the leads 4 are stored in the memory 92. In this case, the opening diameters of the respective diaphragms 50, 51 and 52 and the rotational amount of the output shaft of the Z-direction drive motor 29 are also stored in the memory 92, so that they will be used during the inspection. The "alignment points" includes a total of four points, which are as shown in FIG. 15, for example, two points 2a and 2b on the semiconductor chip 1 and two points 4a and 4b on the lead 4.

First, the inspection of the alignment points 2a and 2b on the semiconductor chip 1 and the alignment points 4a and 4b on the lead 4 in the sample 6 will be described.

When these alignment points are inspected, the ring-form illumination assembly 60 is not switched on, but the vertical illuminator 38 is switched on, thus creating a bright visual field for the sample 6 in order to stabilize the positional correction of the alignment points (2a, 2b, 4a, 4b) at a high level of precision. In addition, the high-magnification camera 44 is used. The opening diameter of the diaphragm 51 is set small, and the opening diameter of the diaphragm 50 is also set small, thus creating a large focal depth.

After these preparations, the sample 6 that is the object of inspection is placed on the inspection stand 10. Then, the X-Y table 22 is moved in accordance with the coordinates of the alignment point 2a of the semiconductor chip 1, which are stored in the memory 92 beforehand as described above, thus positioning the center of the objective lens group 24 roughly over the alignment point 2a so that the alignment point 2a of the sample 6 is located. At this time, the Z-direction drive motor 29 is also actuated to the stored position, thus causing the objective lens group 24 to be moved up and down so that the image of the alignment point 2a that is to be taken in by the objective lens group 24 is focused. In other words, by actuating the Z-direction drive motor 29, the objective lens group 24 is raised or lowered by the cam 30 via the roller 28 and the roller supporting plate 27. In addition, the light from the vertical illuminator 38 is directed onto the area near the alignment point 2a via the diffusing plate 37, the diaphragm 50, the illumination-use lens group 36, the first half-prism 35 and the objective lens group 24.

The image of the alignment point 2a and its surrounding area are picked up by the high-magnification camera 44 via the objective lens group 24, the first half-prism 35, the diaphragm 51, the second half-prism 39, the high magnification imaging lens group 42 and the mirror 43. This image is processed by the image processing unit 90, displayed on the monitor 91, and also stored in the memory 92 by the main controller 93.

The other alignment points 2b, 4a, and 4b are also detected in the same manner as the point 2a is detected as described above.

As a result, the positional coordinates of the respective pads 2 and leads 4 are corrected by the main controller 93 based upon the positional coordinates of the detected alignment points 2a, 2b, 4a, and 4b.

When the inspection of the alignment points 2a, 2b, 4a, and 4b are performed, the conditions (that is, the opening diameters) of the electrically operated diaphragms 50, 51 and 52, the intensity of the vertical illuminator 38 and the rotational amount of the (output shaft of the) Z-direction drive motor 29 (in other words, the position of the objective lens group 24), etc. that are used are those that are initially set and stored in the memory 92 as described above.

Usually, due to the presence of the paste between the semiconductor chip and the lead frame, the heights of the semiconductor chips vary (chip to chip) by approximately 20 to 30 microns. In addition, the surfaces of the semiconductor chips are slightly inclined with respect to the horizontal direction. In order to detect this height discrepancy, the X-Y table 22 and/or the Z-direction drive motor 29 are/is actuated so as to perform automatic focusing. In this case, the X-Y table 22 is driven so that the objective lens group 24 is moved to three previously inputted points (e.g., 2a, 2c and 2b) on each semiconductor chip 1 and the Z-direction drive motor 29 is actuated so that objective lens group 24 focuses the chip 1. Then, the respective detected height values (i.e., rotational amount of the Z-direction motor 29) are stored by the main controller 93.

There are various different methods in automatic focusing referred to above. In this embodiment, the automatic focusing is accomplished by the use of a combination of a pattern matching method and a histogram method. More specifically, the opening diameter of the electrically operated diaphragm 51 is set large so that the focal depth for the objective lens group 14 is shallow. Then, using the pattern matching value (that is obtained while moving the objective lens group 24±50 microns from the stored rotational amount of the Z-direction drive motor 29) and the histogram of the image obtained at this time, the maximum value is taken as a focus matching.

The focus matching at the position where the ball 5a is bonded (i.e., the rotational amount of the Z-direction drive motor 29) is ascertained from the differences in the heights detected between the three points on the surface of the semiconductor chip 1 and the size of the semiconductor chip 1. Accordingly, the inspection of the ball 5a (described below) can be accomplished by moving the objective lens group 24 to the position of the ball 5a via the X-Y table 22 and the Z-direction drive motor 29.

The ball, the crescent and the wire of a bonded wire in a sample will be described below. As an example, the inspection of the ball 5a, the crescent 5b and wire 5A will be described.

When the ball 5a is inspected, the X-Y table 22 is driven so that the center of the objective lens group 24 is brought to coincide with the corrected position of the ball 5a. Such a corrected position is one that is corrected via the main controller 93 based upon the discrepancies of the alignment points as described above. Also, in view of the shape and material (gold mirror surface) of the ball, the vertical illuminator 38 is used so that the ball 5a can appear darker in a bright visual field.

In other words, when the ball 5a is inspected, the vertical illuminator 38 is switched on, and the ring-form illumination assembly 60 is not switched on. The opening diameters of the electrically operated diaphragms 50 and 51 are set somewhat small.

By setting the opening diameter of the diaphragm 50 to be small, the lights from the vertical illuminator 38 becomes parallel and are directed perpendicularly onto the sample 6. On the other hand, if the opening diameter of the diaphragm 50 is set large, the lights from the vertical illuminator 38 is obliquely directed onto the sample 6. Thus, the appearance of the image of the sample 6 can vary by changing the size of the opening diameter of the diaphragm 50.

Figure 7:
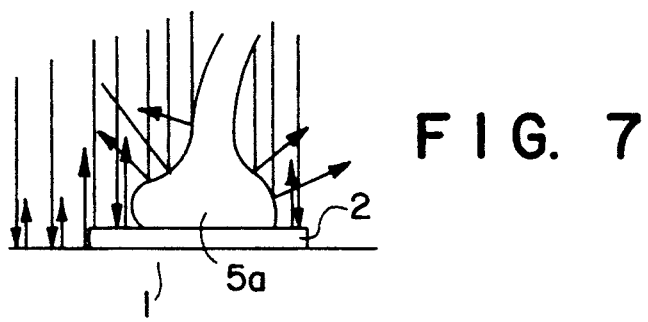
FIG. 7 illustrates the illumination of light onto the ball of a bonded wire.

As described above, the lights from the vertical illuminator 38 pass through the diffusing plate 37, the diaphragm 52, the illumination lens group 36, the first half-prism 35 and the objective lens group 24 and then perpendicularly illuminate the ball 5a as shown in FIG. 7.

The pad 2 surrounding the ball 5a is generally a vacuum-evaporated aluminum. Therefore, when the inspection is performed under a bright visual field by way of the vertical illuminator 38, the pad 2, due to its surface conditions, provides considerable irregular reflection. On the other hand, the surface of the ball 5a is in an Au mirror surface state; therefore, due to its shape as well, the ball 5a provides little irregular reflection.

As a result, the ball 5a appears darker (black) relative to its surroundings, and therefore, the shape of the ball 5a is clearly reproduced by the high-magnification camera 44 via the objective lens group 24, the first half-prism 35, the diaphragm 51, the second half-prism 39, the diaphragm 52, the high-magnification imaging lens group 42 and the mirror 43.

When the shape of the ball 5a is inspected, a black shadow is sought using a commonly used image processing technique, so that the surface area, the center of gravity and the radius of the ball 5a are determined.

Figure 8:
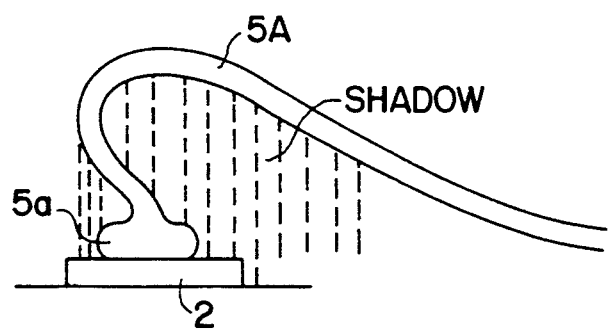
FIG. 8 illustrates a problem (shadow) that would occur in the illumination shown in FIG. 7.
Figure 9A:
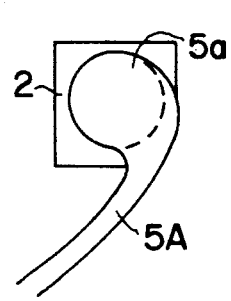
FIGS. 9(a), 9(b), and 9(c) show diagrams of images obtained under the problem of FIG. 8.
Figure 9B:
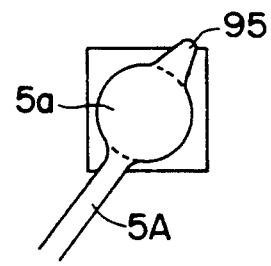
Figure 9C:
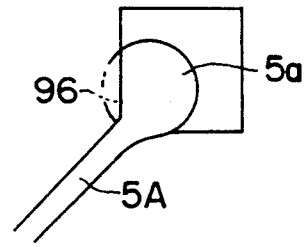

In the above-described embodiment, the ball 5a is made to appear dark using the vertical illuminator 38. Also, the inspection is performed with the opening diameter of the electrically operated diaphragm 51 set large, thus creating a deep focal depth. As a result, the area that the wire 5A occupies (as shown in FIG. 8) and the edges of the pad 2 (as shown in FIG. 9(a)) appear dark, and therefore, the diameter of the ball is not detected correctly. Furthermore, as shown in FIG. 9(b), the shadow 95 of the wire is imaged though it should not; while as shown in FIG. 9(c), the portion 96 of the ball 5a that is beyond the boundary of the pad 2 would not be reproduced though it should be.

Accordingly, a method of obtaining a correct reproduction of the ball 5a only will be described below.

In this case, only the outer ring-form illuminator 65 (which has a low illumination angle) of the ring-form illumination assembly 60 is switched on and used. The vertical illuminator 38 and the inner ring-form illuminator 63 (which has a high illumination angle) of the ring-form illumination assembly 60 are not switched on. Thus, the inspection is performed by brightening the ball 5a in a dark visual field created by these illumination elements. In addition, the opening diameter of the electrically operated diaphragm 51 is set large, so that a shallow focal depth is created.

Figure 10:
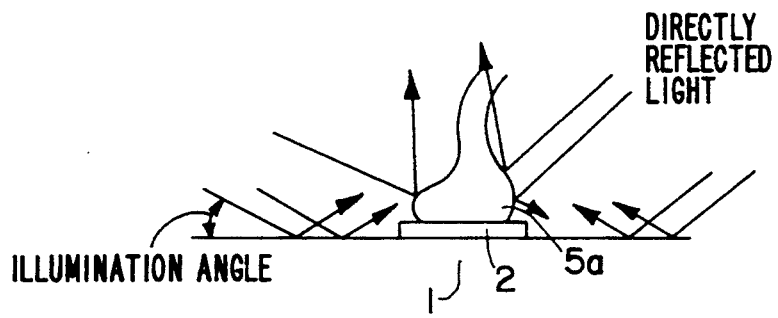
FIG. 10 shows the illumination of light by the ring-form illumination assembly onto the ball of the bonded wire.

More specifically, as shown in FIG. 10, when the ball 5a is illuminated by the outer ring-form illuminator 65 from a low angle of approximately 5 to 15 degrees, a considerable amount of directly reflected light from the ball 5a enters the objective lens group 24, and as a result, the ball 5a appears bright and can be imaged and reproduced. However, because the surface of the semiconductor chip 1 is more or less in a mirror surface state, the light reflected by the surface of the semiconductor chip 1 does not enter the objective lens group 24, and as a result, the surface of the semiconductor chip 1 appears dark.

Figure 11:
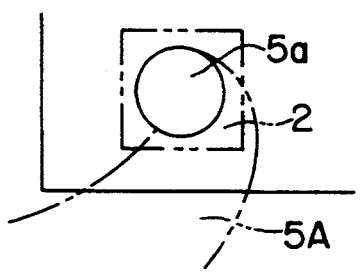
FIG. 11 shows the shape of the ball detected under the illumination shown in FIG. 10.

In addition, by setting the opening diameter of the diaphragm 51 large so as to create a shallow focal depth, and by driving the Z-direction drive motor 29 so that the focal length is matched with the surface of the semiconductor chip 1, there is little reflected light from the wire 5A, and therefore, as shown in FIG. 11, the wire 5A is not imaged, and only the ball 5a appears bright.

In other words, by creating a dark-field illumination circumstance around the ball 5a, it is possible to darken everything including the pad 2 but not the ball 5a that projects from the surface of the semiconductor chip 1. Thus, only the ball 5a can appear bright. In addition, by setting the opening diameter of the diaphragm 51 large and creating a shallow focal depth, the shadow of the wire 5A that appears above the ball 5a can be eliminated. Also, the illumination is provided only by the monochromatic light emitted by the LED's 64 of the outer ring-form illuminator 65; as a result, the focal depth can be as shallow as approximately 10 to 20 microns.

The thus obtained shape of the ball 5a is inspected via image processing, and therefore, an accurate ball diameter is ascertained.

Peelings, floating, etc. of the ball at the end of a bonded wire have been considered impossible to detect in the past. However, these defects appear as indistinct images of the edge of the ball in the present invention, and therefore, are recognizable.

Next, the inspection of the crescent 5b of the wire 5A will be described.

In this case, the X-Y table 22 is driven so that the center of the objective lens group 24 is brought to coincide with the corrected position of the crescent 5b. The inspection of the crescent 5b is performed under a bright visual field as in the same manner as the inspection of the ball 5a. In other words, the inspection is performed with the vertical illuminator 38 switched on. However, since the lead 4, on which the crescent 56 exists, has more surface irregularities than the semiconductor chip 1, not only the lead 4 but also the crescent 5b tend to appear dark. Accordingly, in the crescent inspection, the electrically operated diaphragm 50 is opened wide so that the angled illumination from the vertical illuminator 38 is also used as shown in FIG. 12.

If necessary, the inner ring-form illuminator 63 of the ring-form illumination assembly 60 is switched on, and the outer ring-form illumination 65 is switched off. When illuminated perpendicularly by the vertical illuminator 38, the crescent 5b provides lesser irregular reflected light that the lead 4; therefore, the crescent 5b appears dark. However, since there are indentations and projections on the lead 4, illumination by the vertical illuminator 38 creates brightness irregularity on the lead 4. Accordingly, the crescent 5b is illuminated from an angle of approximately 30 to 55 degrees by the use of the inner ring-form illuminator 63 of the ring-form illumination assembly 60, so that the brightness irregularity on the lead 4 caused by the illumination by the vertical illuminator 38 is eliminated.

Figure 12:
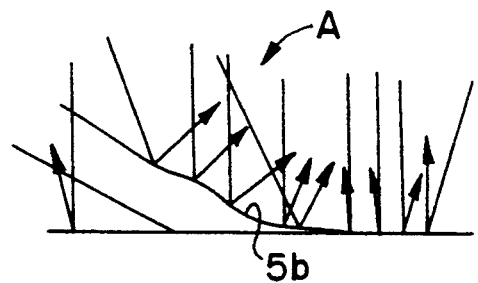
FIG. 12 shows the illumination of light onto the crescent of the wire.

However, the illumination provided by all the LED's 62 of the inner ring-form illuminator 63 from the direction indicated by arrow A in FIG. 12 (i.e., from the direction of the lead 4 to which the crescent 5b to be inspected is bonded) brightens only a portion of the crescent 5b. Thus, a correct entire shape of the crescent 5b is not imaged. In order to avoid this, some LED's 62 which illuminate the crescent 5b from the direction indicated by arrow A are switched off. In other words, the LED group 62A shown in FIG. 4 is turned off. This is accomplished via the illumination switching circuit 50 shown in FIG. 5.

More specifically, the respective shift registers of the shift register group 85 are successively switched by the clock signal 88; and in each case, a high (on) or low (off) input signal 87 is inputted; the high or low input signal 87 is successively stored in each register of the shift register group 85 via the clock signal 88; and then the signal stored in each register is transferred to the latch register group 84 via the load signal 86. As a result, the LED group 62A that illuminate the crescent 5b from the direction indicated by arrow A is not turned on. Which LED's 62 are to be switched off is designated beforehand by a program stored in a control circuit (not shown) in accordance with the object to be inspected.

Accordingly, as described in the inspection of the ball 5a, the crescent 5b is clearly reproduced by the high-magnification camera 44 via the objective lens group 24, the first half-prism 35, the diaphragm 51, the second half-prism 39, the diaphragm 52, the high magnification imaging lens group 42 and the mirror 43.

Lastly, the inspection of the presence, linearity and height of the wire 5A will be described.

The presence and linearity of the wire 5A is inspected after the ball 5a and the crescent 5b have been inspected by the methods as described above. This presence and linearity inspection of the wire 5A is accomplished by the image processing unit 90; in other words, the image processing unit 90 processes a bright line that appears between the ball 5a and the crescent 5b. In this inspection, the vertical illuminator 38 and the inner ring-form illuminator 63 of the ring-form illumination assembly 60 are not switched on, and only the outer ring-form illuminator 65 is switched on. The opening diameter of the diaphragm 51 is set small.

If the vertical illuminator 38 is on, the reflected light from the area surrounding the wire 5A (i.e., the semiconductor chip 1, lead 4 and paste 7) will enter the low-magnification camera 41 to a greater extent than the reflected light from the wire 5A, thus brightening such a surrounding area, resulting in that the wire 5A does not appear bright. The reason for this is that the surface of the bonding wire is in an Au mirror surface state, and there are various bright and dark spots in the area surrounding each wire. Accordingly, when the wire is inspected, it is necessary, in order to increase the precision of inspection as well, to darken the entire area that surrounds the wire and brighten the wire only. For this reason, the vertical illuminator 38 is not turned on nor used. In addition, the angle of incidence of the light from the LED's 62 of the inner ringform illuminator 63 is as large as approximately 45 degrees; as a result, there is considerable reflected light from an area other than the wire 5A if the inner ring-form illuminator 63 is on. For this reason, the inner ring-form illuminator 63 is not turned on nor used.

Experiments show that illumination at an angle of incidence of light of approximately 5 to 15 degrees is the most appropriate for making the wire alone appear bright. When such a small angle of incidence of light is used, directly reflected light from the area other than the wire is extremely small.

However, if the wire 5A is illuminated by all the LED's 64 of the outer ring-form illuminator 65, some portions of the wire 5A are obscured by the paste 7. Accordingly, the LED group 64A that provides illumination from the direction indicated by arrow A (i.e., from the side of the lead 4 to which the wire 5A being inspected is bonded) is turned off as in the case of inspection of the crescent 5b (in which the LED group 62A is turned off). As a result, the wire 5A can be clearly reproduced by the low-magnification camera 41. The positions of the ball 5a and the crescent 5c are already known and stored in the image processing unit 90 as described above; thus a bright line that appears between the ball 5a and the crescent 5c and represents the wire 5A can be easily traced. Thus, the presence and linearity of the wire 5A is inspected.

The height of the wire 5A is inspected as described below. In the wire height inspection, the electrically operated diaphragm 51 is opened, and the low-magnification camera 41 is used.

Figure 13:
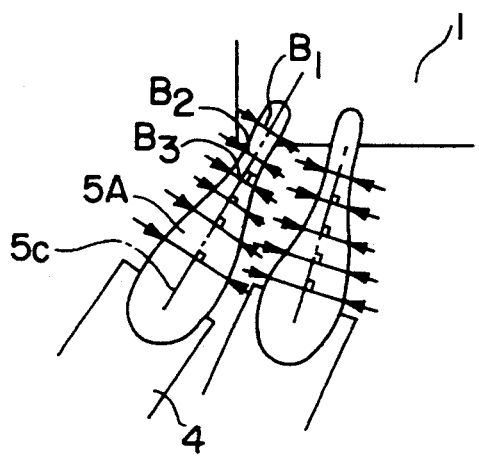
FIG. 13 illustrates the wire height inspection, wherein the focus is on the semiconductor chip.
Figure 14:
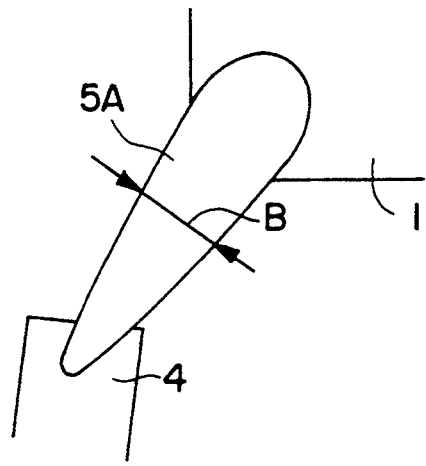
FIG. 14 illustrates the wire height inspection, wherein the focus is brought into the lead.
Figure 19:
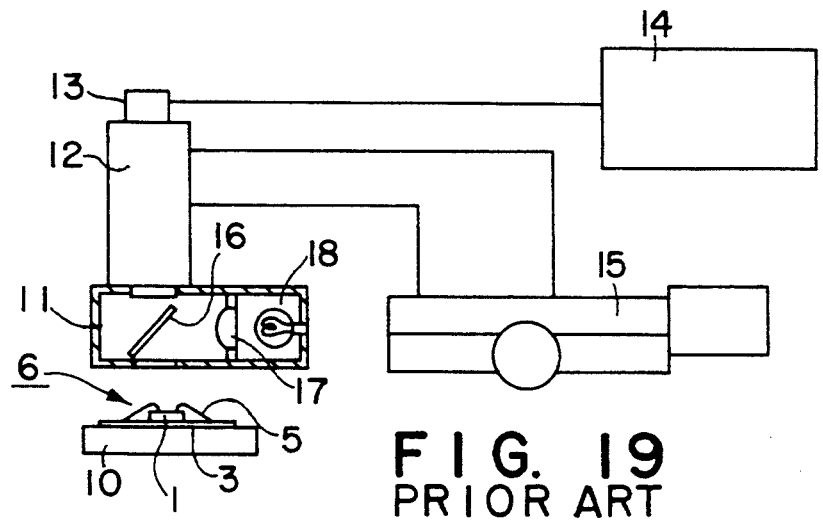
FIG. 19 is a structural diagram of a conventional bonding wire inspection apparatus.

By opening the diaphragm 51, the focal depth of the objective lens group 24 becomes shallow. Accordingly, when the focus of the objective lens group 24 is brought into the semiconductor chip 1, the image of the wire 5A is obtained by the low-magnification camera 41 via the objective lens group 24, the first half-prism 35, the diaphragm 51, the second half-prism 39 and the low-magnification imaging lens group 40 and then processed by the image processing unit 90. The thus processed image appears as shown in FIG. 13. On the other hand, when the focus of the object lens group 24 is brought into the lead 4, the image of the wire 5A appears as shown in FIG. 14; in other words, the wire 5A appears indistinctly and differently in the width. For this reason, the widths that are at right angles to a (imaginary) line $5c$, that represents the presence of the wire, between the ball $5a$ and the crescent $5b$ (which has been confirmed by the inspection of the wire as described above), in other words, the indistinct-image widths $B_1$, $B_2$, $B_3$ ..., are measured by the main controller 93.

Experiments show that there is a constant relationship between the indistinct-image widths and the height of a wire as obtained by the Equation below:

Height to be Determined = K × (Indistinct-Image Width at Point Where Height is Determined — Wire Width)

In the above Equation, the "Height to be Determined" refers to the height of wire from, in this embodiment, the focal position of the objective lens group 24 that is calculated from the rotational amount of the Z-direction drive motor 29 at the time of the inspection. In addition, "K" in the Equation is a proportionality constant.

Accordingly, by measuring the indistinct image with the main controller 93, the height at any desired point of the wire 5A can easily be measured.

However, if the indistinct image width becomes larger, the difference in the relative brightness between the indistinct image and its surrounding area becomes smaller, thus making the recognition of the wire difficult. In this case, the Z-direction drive motor 29 is actuated, and the focal position of the objective lens group 24 is shifted from its position on the semiconductor chip to a position on the lead in order to take in an indistinct image of the wire 5A based upon the focal position on the lead 4.

By combining the indistinct image of the wire with the focal position set on the semiconductor chip and the indistinct image of the wire with the focal position set on the lead frame, a precise recognition of the wire is obtained. That is to say, the image in the vicinity of the focus has greater contrast; accordingly, the difference between the indistinct image and its surroundings (i.e., the edges of the indistinct image) can be more easily determined.

As seen from the above, when the focus of the objective lens group 24 is brought into or set on the semiconductor chip 1, the image of the wire 5A, that has been image-processed by the image processing unit 90 based upon the image taken thereinto via the low-magnification imaging lens group 40 and the low-magnification camera 41, is indistinct (vignette) with differences in width. Thus, such an indistinct image width is measured by the main controller 93.

Experiments show that there is a constant relationship between the indistinct image widths and the height of a wire as seen from the equation above. Accordingly, by measuring the indistinct image width by the main controller 93, the height of any desired point of the wire 5A can be easily measured.

However, if the indistinct image width is large, the difference in the relative brightness between the indistinct image and its surrounding area becomes smaller, which results in that the recognition of wire is difficult. In this case, the Z-direction drive motor 29 is actuated so that the focal position of the objective lens group 24 is shifted from its position on the semiconductor chip to a position on the lead in order to take in an indistinct image based upon the focal position on the lead 4.

By using the combination of the indistinct images that are taken with the focuses on the semiconductor chip and on the lead frame, a more precise recognition becomes possible.

In the above described embodiment, only the objective lens group 24 is moved up and down when conducting focusing, but the focusing can be done by moving the opto-head 23 as a whole up and down or moving the inspection stand 10 up and down.

As seen from the above, according to the present invention, the focus of the optical means is first set on a desired point of the object of inspection (that is, the bonded wire), thus setting the height of such a point as a reference; then the image of the object thus focused is photographed by a camera; and then the height of the object is calculated based upon the width of the indistinct image thus photographed. Thus, the inspection method of the present invention requires fewer focusing actions to measure the height of the object, greatly reducing the measuring time.

I claim:

1. A method of inspecting wires bonded between pads of a semiconductor chip and leads of a lead frame, said method comprising the steps of:

moving a single optical means in a Z direction to focus said single optical means onto a surface of a semiconductor chip with a desired lead and desired bonding wire within an image field of said single optical means, said single optical means comprising a low magnification camera with a shallow depth of focus;

photographing an indistinct image of said desired bonding wire;

measuring a width of said indistinct image of said desired bonding wire;

moving said single optical means in said Z direction to focus said single optical means onto a lead;

photographing an indistinct image of said desired bonding wire;

measuring a width of said indistinct image of said desired bonding wire; and calculating a height of said desired bonding wire from said measured widths of said indistinct image of said desired bonding wire when said single optical means is focused on said surface of said semiconductor chip and focused onto said lead;

whereby a more precise measurement of the height of said bonding wire is made.

2. The method of according to claim 1 further comprising a ring form illumination means for illuminating said semiconductor chip, bonding wire and lead.

3. The method according to claim 1, wherein a width of said indistinct image is measured at a plurality of locations and a plurality of heights of said bonding wire are calculated from said plurality of measurements.

* * * * *